(12) United States Patent
Hess

(10) Patent No.: US 6,974,433 B2
(45) Date of Patent: Dec. 13, 2005

(54) TUBULAR COMPRESSION BANDAGE

(75) Inventor: Heinrich Hess, Kleinblittersdorf (DE)

(73) Assignee: Bauerfeind AG, Zeulenroda (DE)

( * ) Notice: Subject to any disclaimer, the term of this patent is extended or adjusted under 35 U.S.C. 154(b) by 24 days.

(21) Appl. No.: 10/805,495

(22) Filed: Mar. 22, 2004

(65) Prior Publication Data

US 2004/0249329 A1 Dec. 9, 2004

(30) Foreign Application Priority Data

Mar. 21, 2003 (DE) .......................... 103 12 656

(51) Int. Cl.$^7$ ............................................. A61F 13/00
(52) U.S. Cl. .............................. 602/63; 602/60; 602/61; 602/62
(58) Field of Search ............................ 2/239, 240, 455, 2/22; 602/20, 23, 26, 60–63; 128/882

(56) References Cited

U.S. PATENT DOCUMENTS

| | | | |
|---|---|---|---|
| 3,831,487 A | | 8/1974 | Moore |
| 3,856,008 A | * | 12/1974 | Fowler et al. ................. 602/62 |
| 3,926,186 A | | 12/1975 | Nirschl |
| 4,215,687 A | * | 8/1980 | Shaw .......................... 602/60 |
| 4,366,813 A | | 1/1983 | Nelson |
| 4,941,462 A | * | 7/1990 | Lindberg ..................... 602/16 |
| 5,016,621 A | | 5/1991 | Bender |
| 5,254,122 A | | 10/1993 | Shaw |
| 5,277,697 A | * | 1/1994 | France et al. ................. 602/16 |
| 5,512,039 A | * | 4/1996 | White .......................... 602/26 |
| 5,653,244 A | * | 8/1997 | Shaw .......................... 128/882 |
| 5,743,866 A | | 4/1998 | Bauerfeind et al. |
| 5,873,848 A | * | 2/1999 | Fulkerson .................... 602/62 |
| 6,063,048 A | * | 5/2000 | Bodenschatz et al. ........ 602/62 |
| 6,080,121 A | | 6/2000 | Madow et al. |
| 6,142,965 A | * | 11/2000 | Mathewson .................. 602/62 |
| 6,425,876 B1 | | 7/2002 | Frangi et al. |

FOREIGN PATENT DOCUMENTS

| | | | | |
|---|---|---|---|---|
| DE | 4013693 A1 | * | 8/1991 | ............. A61F/5/04 |
| DE | 199 50 509 | | 11/2001 | |
| EP | 611069 A1 | * | 8/1994 | ............. A61F/5/01 |
| EP | 0860153 | | 8/1998 | |
| WO | WO8801855 | * | 3/1988 | |
| WO | WO9400082 | * | 1/1994 | |
| WO | WO9836713 | * | 8/1998 | |
| WO | WO 01/03624 | | 1/2001 | |

* cited by examiner

*Primary Examiner*—Kim M. Lewis
(74) *Attorney, Agent, or Firm*—Banner & Witcoff, Ltd.

(57) ABSTRACT

A tubular compression bandage of elastic textile material includes a plurality of tightening straps adjacently encompassing the bandage. The tightening straps are fastened by their starting portions to a starting longitudinal strip connected to the outer surface of the bandage and are guided circumferentially in pairs at an oblique angle of up to 30° with respect to the longitudinal direction of the bandage to their terminating portions of the side opposite the starting longitudinal strip to pairs of securing eyes arranged in herringbone-like manner and are folded back therein to form Velcro™ fasteners on the bandage, the degree of oblique guiding being adjustable through selectble fixing of the starting and/or terminating portions of the tightening straps in the longitudinal direction of the bandage.

5 Claims, 3 Drawing Sheets

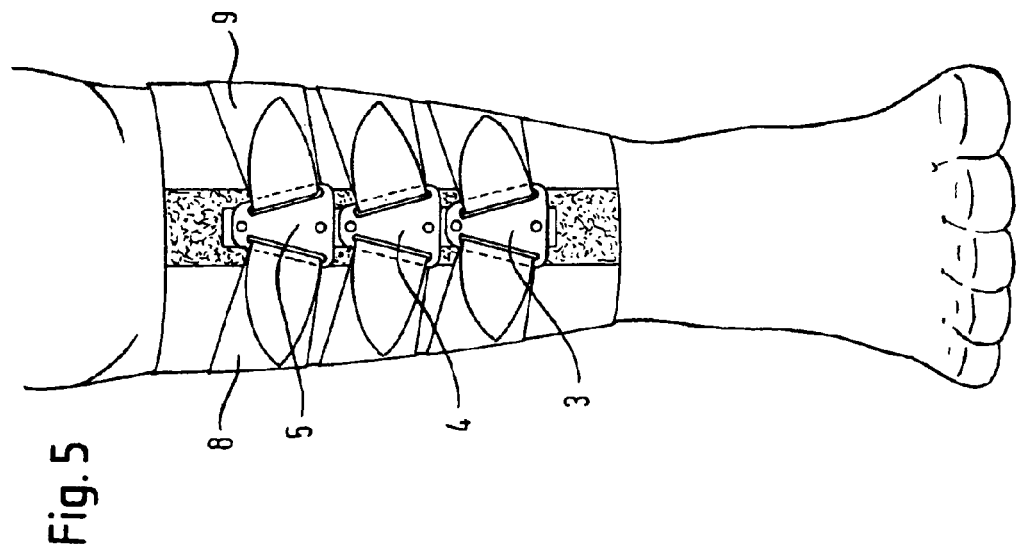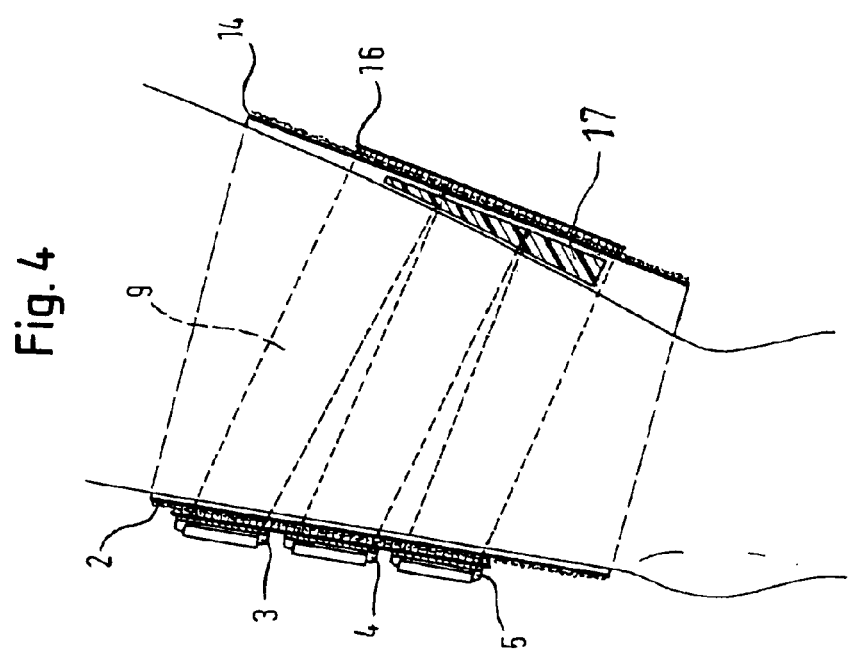

TUBULAR COMPRESSION BANDAGE

The invention relates to a tubular compression bandage of elastic textile material, the compression bandage being provided with a plurality of tightening straps adjacently encompassing the bandage.

Such a bandage is disclosed, for example, in German patent specification 44 19 260. The tightening straps fitted to the said bandage each extend in the circumferential direction over a short length of the bandage and serve to pull together more or less strongly that portion bridged by them. When the tightening straps are tightened, this bandage allows a pressure issuing radially inwards from the bandage to be exerted on the respective body part, wherein, owing to the direction of the tightening straps extending in the circumferential direction of the bandage, the bandage is able to exert exclusively the said pressure.

Bandages with more or less widely encompassing tightening straps are available in a variety of designs in the prior art. Reference may be made in this connection, for example, to the PCT specification WO 01/03624, which relates in FIG. 2 to a longitudinally slitted bandage with virtually completely encompassing tightening straps in exclusively the circumferential direction. U.S. Pat. No. 3,856,008 likewise discloses a longitudinally slitted bandage in which the longitudinal slit is bridged by circumferentially extending tightening straps in order, through selectable attachment of the straps, to exert a variable, radially extending pressure on the respective body part. U.S. Pat. No. 4,366,813 discloses a tubular bandage for the knee joint in which, for the purpose of concentrating the action of the bandage on the knee joint both above the knee joint and also below the knee joint, tightening straps are fitted which extend approximately at an angle of 45°, said tightening straps being directed in opposite directions such that the forces exerted by the diagonally extending tightening straps are mutually compensated, as a consequence of which the bandage is secured against moving and is held in position in the region of the knee joint.

Compression bandages are used in particular when there is an injury to muscle fibres and in particular, therefore, a torn muscle. In the treatment of such injuries, it has been shown that bandages, especially bandages fitted in order to prevent bruising, which exert exclusively radially inwardly directed pressure do not lead to optimal results.

The object of the invention, therefore, is to create a tubular compression bandage of the initially described design in which the therapeutic effect is considerably improved in comparison with the known bandages. The object of the invention is achieved in that the tightening straps are fastened by their starting portions to a starting longitudinal strip connected to the outer surface of the bandage and are guided circumferentially in pairs at an oblique angle of up to 30° with respect to the longitudinal direction of the bandage to their terminating portions on the side opposite the starting longitudinal strip to pairs of securing eyes arranged in herringbone-like manner and are folded back therein to to mate with a hook and loop fastener element to form, for example, Velcro™ fasteners on the bandage, the degree of oblique guiding being adjustable through selectable fixing of the starting and/or terminating portions of the tightening straps in the longitudinal direction of the bandage.

In the bandage according to the invention, an inwardly directed pressure is combined with a pressure acting in the longitudinal direction of the respective body part, because, namely, the oblique guiding of the tightening straps, which in any case exert an inwardly directed pressure, gives rise in the treated body part to an additional pressure acting in the longitudinal direction thereof, said additional pressure acting in the respective direction of the muscle fibres and ensuring that the muscle fibres are pulled together. Upon application of the said bandage in a region situated substantially also adjacent to the actual injury site, the bandage exerts a pulling effect on the respective body part, said pulling effect extending in the direction of the muscle fibres and ensuring that the injured region is given the tendency to be pushed together, this denying an emerging blood clot the therefor required space and keeping the emerging scar as small as possible, so that the muscle function is disturbed as little as possible.

The strength of the pulling effect exerted on the respective body part and extending in the longitudinal direction thereof depends on the degree of oblique guiding of the tightening straps, which preferably should be guided at up to 30° with respect to the longitudinal direction of the bandage. The selectable fixing of the starting and/or terminating portions of the tightening straps in the longitudinal direction of the bandage makes it possible for the bandage, immediately when being fitted, to adapt to the respective body part, as required by the shape of the respective body part, it being possible, therefore, for the thickness of the body part and, where applicable, the conical form thereof to be directly taken into consideration and it thus also being possible for the necessary pulling effect on the respective body part to be selectably adjusted with regard to the force thereof.

For the selectable fixing of the starting portions of the tightening straps, the pairs of securing eyes can be fixed as a row in the longitudinal direction of the bandage to a terminating longitudinal strip secured to the bandage, the securing eyes being fixed in a selectable position with respect to the longitudinal direction of the bandage.

Similarly, the starting longitudinal strip, to which the tightening straps are connected by their starting portions, may be in the form of a Velcro™ strip. This makes it possible suitably to vary the degree of oblique guiding of the tightening straps. Such fixing can be effected either just with regard to the starting portions of the tightening straps or with regard to the terminating portions of the tightening straps or with regard to both portions of the tightening straps.

Additional treatment of an injured muscle using the compression bandage according to the invention can be achieved in that said bandage is provided with a pressure pad, this being advantageously possible in that the bandage is provided on its inner surface with a Velcro™ layer, it being possible for a pressure pad with Velcro™ fastening portions to be selectably attached to said Velcro™ layer. Depending on the site of the injury covered by the compression bandage, the pressure pad is then additionally inserted and then exerts a supplementary pressure on the injured site in addition to the tensile and compressive forces exerted by the bandage.

The selectable positioning of the pad makes it possible for the pad, prior to its insertion in the bandage, to be provided with a cooling medium, e.g. ice-cold water, the pad soaking up said medium, this, as is known, being constantly applied in the treatment of the herein relevant injuries.

An illustrative embodiment of the invention is presented in the drawings, in which:

FIG. 1 shows the compression bandage with a view of the pairs of securing eyes and relatively pronounced oblique guiding of the tightening straps;

FIG. 2 likewise shows a view of the pairs of securing eyes with a lesser degree of oblique guiding of the tightening straps;

FIG. 4 shows a section through the bandage, fitted to a thigh according to line I—I from FIG. 1;

FIG. 5 shows the compression bandage fitted to a lower leg with a view onto the pairs of securing eyes;

Figure 1:
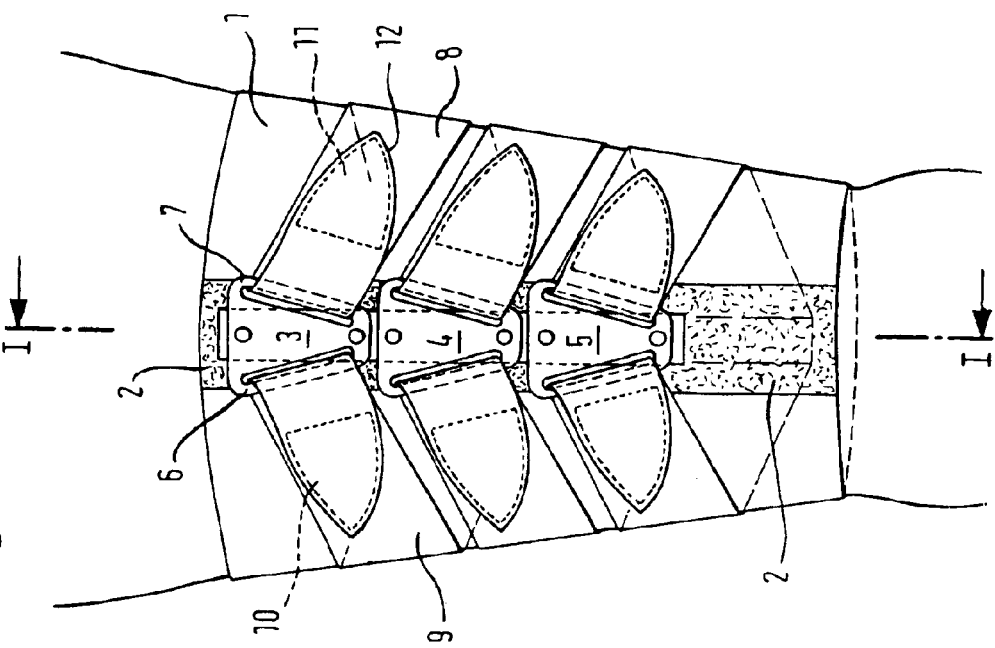

The tubular compression bandage presented in FIG. 1 consists of the tube piece 1 made of elastic textile material, attached to the front side of which on the outside is the starting longitudinal strip 2, which extends in the longitudinal direction of the bandage. Fastened on the starting longitudinal strip 2 are three securing eye holders 3, 4 and 5 each comprising a pair of securing eyes 6 and 7. The securing eyes 6 and 7 are, as can be seen, positioned at an oblique angle with respect to the longitudinal direction of the bandage, this favouring the oblique guiding of the tightening straps 8 and 9, which are passed through the securing eyes 6 and 7. The three securing eye holders 3, 4 and 5 are attached to the starting longitudinal strip 2 by means of Velcro™ fasteners, for which purpose the starting longitudinal strip 2 is in the form of a pile strip and the securing eye holders 3, 4 and 5 are provided with corresponding hook parts.

The tightening straps 8 and 9 are passed through the securing eyes 6 and 7 and then folded back, the latter likewise being attached to the respective tightening straps 8 and 9 by means of a Velcro™ fasteners 10 and 11, the tightening straps for this purpose being provided with pile layers. FIG. 1 shows how the terminating portion 12 of the tightening strap 8 has initially not yet been completely folded back with its terminating portion 12.

Figure 2:
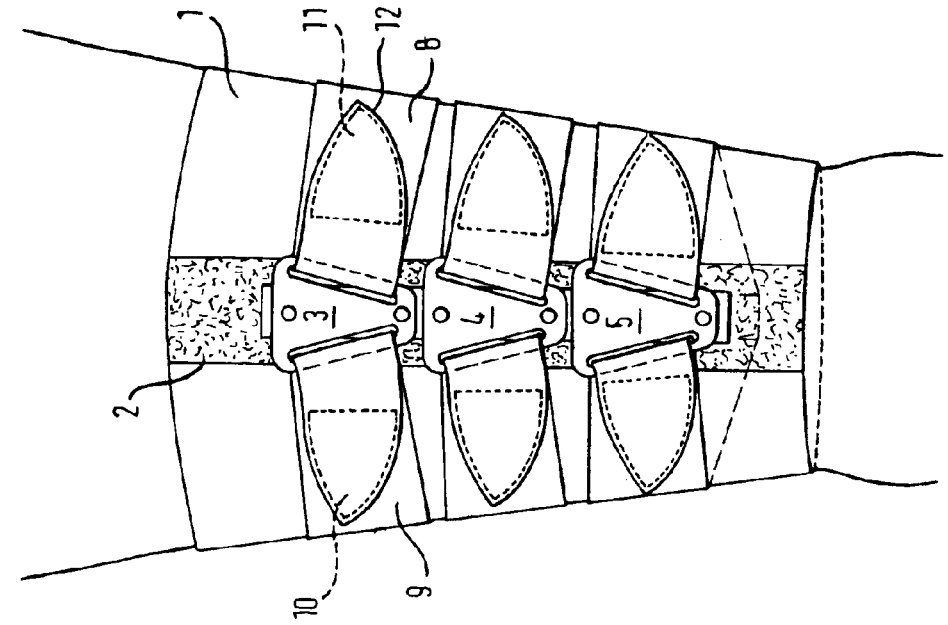

The compression bandage shown in FIG. 2 is broadly identical to the one shown in FIG. 1. However, the compression bandage shown in FIG. 2 is differently adjusted with regard to the oblique guiding of its tightening straps 8 and 9; namely, as a result of corresponding fixing of the securing eye holders 3, 4 and 5 in slightly lower positions, the adjustment is such that the tightening straps 8 and 9 are guided at a less oblique angle than in FIG. 1.

Figure 3:
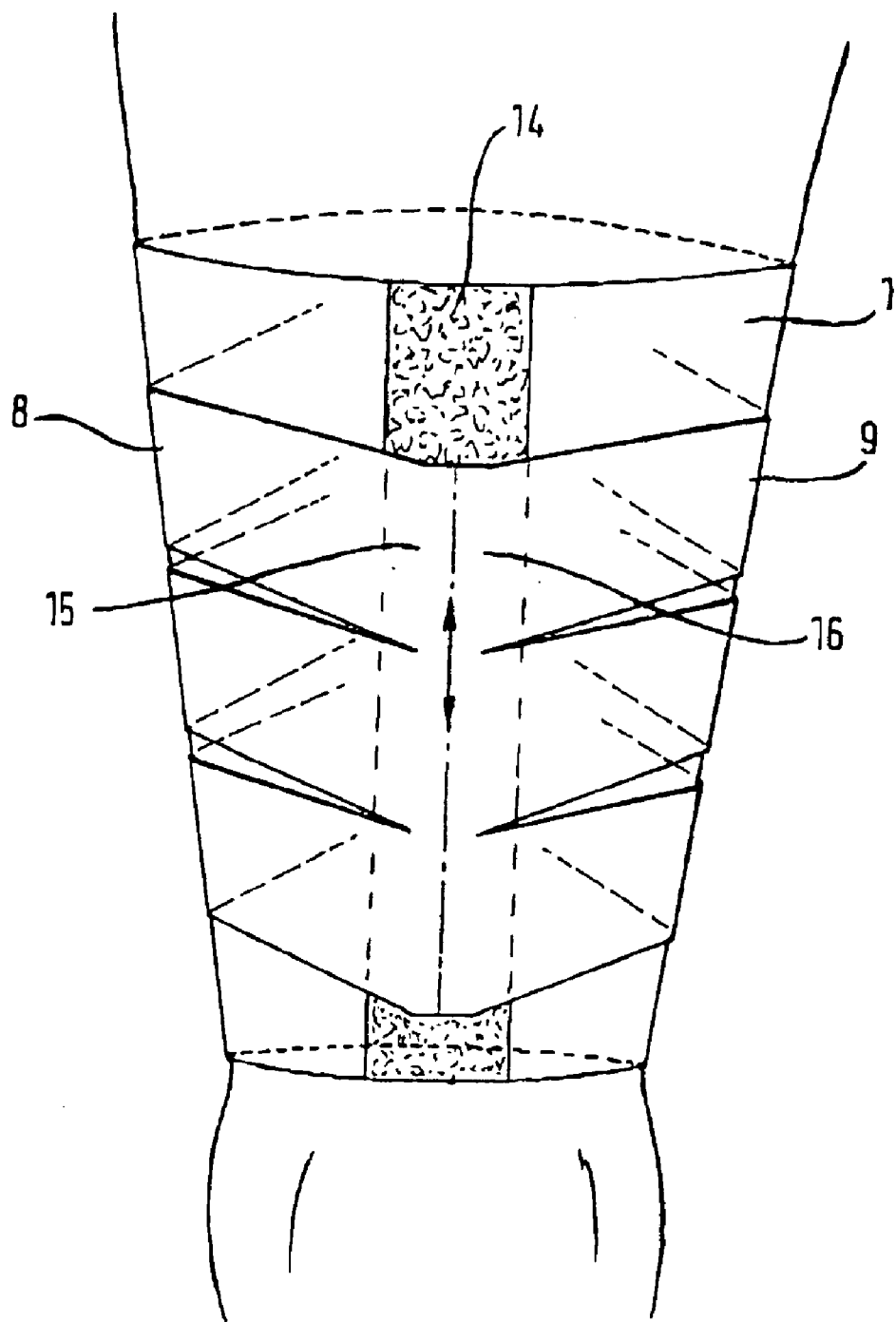
FIG. 3 shows a view of the same bandage, more specifically of the rear side of the bandage with the starting longitudinal strip holding the starting ends of the tightening straps.

FIG. 3 shows the compression bandage presented in FIGS. 1 and 2 with a view onto the rear side thereof, namely onto the starting longitudinal strip 14, to which the starting portions 15 and 16 of the tightening straps 8 and 9 are attached relatively far down on the starting longitudinal strip 14, such attachment being accomplished by means of Velcro™ fastener, this then resulting in a corresponding visible oblique position of the tightening straps 8 and 9 in view of the attachment of the securing eye holders on the other side (see FIGS. 1 and 2).

FIG. 4 presents a section along line I—I from FIG. 1 showing the positions of the tightening straps 9 hidden by the respective body part (in this case, a thigh). The tightening straps 9 extend from the starting longitudinal strip 14 to the securing eye holders 3, 4 and 5, where they are then folded back in the manner shown in FIGS. 1 and 2. The securing eye holders 3, 4 and 5 are fixed on the terminating longitudinal strip 2. Depending on the positions of the securing eye holders 3, 4 and 5 and of the starting portions 16 on the starting longitudinal strip 14, there results a corresponding oblique position of the tightening straps 9; the other starting portions 15 and tightening straps 8 are not visible in the sectional drawing according to FIG. 4. Additionally shown is the pressure pad 17, which is inserted into the bandage in the region of the starting longitudinal strip 14 and which is held in place at the insertion site by a Velcro™ layer provided on the inside of the bandage. Depending on its selectable position, the pressure pad 17 locally exerts a particular pressure on an injury site, this permitting an especially desired treatment of the injury in addition to the effect of the compression bandage.

FIG. 5 presents an illustrative embodiment in order to demonstrate a possible application of the compression bandage according to the invention. In a view of the front side, FIG. 5 shows a bandage fitted to the lower leg. As can be seen in FIG. 5 the tightening straps 8 and 9 are obliquely guided in the manner presented opposite in FIGS. 1 and 2, which means that the lower leg is subjected to a pulling effect of the tightening straps from the bottom rear to the top front.

What is claimed is:

1. A tubular compression bandage comprising:
a tubular compression bandage;
a plurality of tightening straps;
a starting longitudinal strip connected to the outer surface of the bandage; and
a plurality of securing eyes attached to the strip;
wherein the plurality of tightening straps adjacently encompass the bandage;
wherein the tightening straps are removably fastened at their starting portion to the longitudinal strip and are guided circumferentially in pairs at an oblique angle of up to 30° with respect to the longitudinal direction of the bandage to their termination portion on the side of the bandage opposite the starting longitudinal strip through the pairs of securing eyes arranged in a herringbone-type manner and are folded back and fastened to themselves; and
wherein the degree of oblique guiding is adjustable through selective fixing of the starting and/or terminating portion of the tightening straps in the longitudinal direction of the bandage.

2. The tubular compression bandage according to claim 1, wherein the pair of eyes are removably fixed in a row in the longitudinal direction of the bandage to terminating longitudinal strip secured to the bandage.

3. The tubular compression bandage according to claim 2, wherein the terminating longitudinal strip comprises a strip of a hook and loop fastener element.

4. The tubular compression bandage according to claim 1, wherein the starting longitudinal strip comprises a strip of a hook and loop fastener element.

5. The tubular compression bandage according to claim 1, wherein the compression bandage further comprises a layer of a hook and loop fastener element for selective attachment of a pressure pad with a mating hook and loop fastener.

* * * * *